(12) United States Patent
Sangwan et al.

(10) Patent No.: US 6,893,667 B2
(45) Date of Patent: May 17, 2005

(54) PROTEIN PROFILING OF HYPER ACIDIC PLANTS AND HIGH PROTEIN EXTRACTION COMPOSITIONS THEREOF

(75) Inventors: Rajender Singh Sangwan, Lucknow (IN); Neelam Singh Sangwan, Lucknow (IN); Bali Ram Tyagi, Lucknow (IN); Avdhesh Kumar Srivastava, Lucknow (IN); Usha Yadav, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 19 days.

(21) Appl. No.: 10/104,062

(22) Filed: Mar. 22, 2002

(65) Prior Publication Data

US 2003/0180709 A1 Sep. 25, 2003

(51) Int. Cl.$^7$ .......................... A61K 35/78; A01N 37/18
(52) U.S. Cl. ............................................ 424/725; 514/2
(58) Field of Search .............................. 424/725, 195.1; 514/2

(56) References Cited

PUBLICATIONS

Arora et al. Water–Stress–Induced Heat Tolerance in Geranium Leaf Tissues: A Possible Linkage Through Stress Proteins? Physiologia Plantarum vol. 103, No. 1 pp. 24–34.*

* cited by examiner

Primary Examiner—Patricia Leith
(74) Attorney, Agent, or Firm—Ladas & Parry LLP

(57) ABSTRACT

The present invention relates to a method for profiling of protein extract from hyper-acidic aerial parts of plant Scented Geranium (*Pelargonium* sp.), said method comprising steps of selecting effective extraction medium, with extraction medium consisting of 0.2 M sodium carbonate increasing percentage extract by about 600%, selecting effective medium to determine polypeptide pattern in said extract, with polypeptide pattern medium consisting of Sodium Carbonate ranging between 0.2 to 0.4 M, and 0.2 M Sodium Carbonate along with 50% dimethylsulfoxide, selecting effective media to determine enzyme multimolecular forms in said extract, with enzyme multimolecular forms media consisting of 0.2 M Tris-HCl buffer at pH 7.5, and optionally 50% dimethylsulfoxide; Sodium Carbonate at concentration ranging between 0.2 to 0.4 M and optionally 50% dimethylsulfoxide, and using biochemical and biophysical techniques comprising gel electrophoresis, spectrophotometry, centrifugation, protein estimation in said method to determine quantitative, qualitative, structural and functional facets of the proteins from said extract, and extraction compositions thereof.

24 Claims, 2 Drawing Sheets

Figure 1:
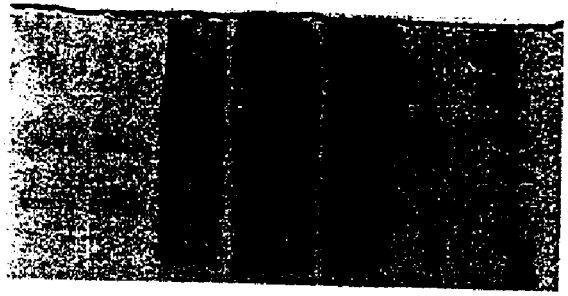

PROTEIN PROFILING OF HYPER ACIDIC PLANTS AND HIGH PROTEIN EXTRACTION COMPOSITIONS THEREOF

FIELD OF THE PRESENT INVENTION

The present invention relates to a method for profiling of protein extract from hyper-acidic aerial parts of plant Scented Geranium (*Pelargonium* sp.), said method comprising steps of selecting effective extraction medium, with extraction medium consisting of 0.2 M sodium carbonate increasing percentage extract by about 600%, selecting effective medium to determine polypeptide pattern in said extract, with polypeptide pattern medium consisting of Sodium Carbonate ranging between 0.2 to 0.4M, and 0.2 M Sodium Carbonate along with 50% dimethylsulfoxide, selecting effective media to determine enzyme multimolecular forms in said extract, with enzyme multimolecular forms media consisting of 0.2M Tris-HCl buffer at pH 7.5, and optionally 50% dimethylsulfoxide; Sodium Carbonate at concentration ranging between 0.2 to 0.4M and optionally 50% dimethylsulfoxide, and using biochemical and biophysical techniques comprising gel electrophoresis, spectrophotometry, centrifugation, protein estimation in said method to determine quantitative, qualitative, structural and functional facets of the proteins from said extract, and extraction compositions thereof.

BACKGROUND AND PRIOR ART REFERENCE

The study of enzymes usually by biochemical methods involves their quantitative and qualitative isolation in active and/or native structural forms followed by analyses/profiling for catalytic levels, enzymes/isozymic molecular forms to discern functional facets, patterning of proteins and/or their polypeptides and their further analyses and constitutes the subject matter of the term 'proteomics'.

The subject has been associated with isolation of nearly wholesome of protein complement from cells, tissues, organs or organisms for the follow-up of identification, characterization and quantitation, electrophoretic display of protein and polypeptide profiles, monitoring of catalytic levels of enzymes and isozymes, discerining multiple molecular forms of enzymes etc.

Today, the proteomics covers much of the functional analysis of gene products or functional genomics. Merely DNA sequences in databases fail to decipher the biological function and hence, proteomics has become crucial for understanding modulating biological functions and mechanisms. For this reason, it is a key component of modern biotechnology including genetic manipulation and metabolic engineering.

In fact, the understanding of the biological functions of genes is a more difficult proposition than obtaining just the sequences. From a plant (particularly those with secondary metabolite producing pathways) perspective, the situation is more complex due to far little known about the metabolic networks and catalytic/regulatory proteins involved.

The most critical requirement in the proteomics initiative is the quantitative isolation of cellular protein complement from the test tissue/organism. Although, some general protocols for isolation of proteins under buffered conditions near neutrality of pH could be available in the literature, however, these can not be satisfactorily applied to several tissues (like leaf, petal and sepal) of scented geranium.

In fact, so far there is only singular report on a male fertile genotype of scented geranium concerning aqueous isolation and profiling of proteins under non-denaturing conditions and that pertains to the anthers only (S. Tokumasu, F. Yano and M. Kato, 1977, Japan J. Genet. 52:197–205).

But this prior art is hardly of any relevance for the larger proteomic work as (i) most of the cultivated clones of scented geraniums are male sterile, (ii) the procedure can not be applied to other aerial parts like leaf, petal and sepal, (iii) rather than anthers, other aerial parts of plant are important for the proteomic work from the standpoint of metabolic pathways and production of valuable exotic essential oil for use in perfumery, cosmetic and flavour industries and aromatherapy (E. Gildemeister and Fr. Hoffman, 1959, Die atherischen Ole vol 5, p 350, Akademie Verlag, Berlin).

The scientific explanation for the invention is that the aerial parts like leaf lamina, sepal and petal of scented geranium are highly acidic in nature with cell sap pH of about 3.0 (R. S. Sangwan, B. R. Tyagi and N. S. Sangwan, 2000, Ecological method of phytoremediation of alkaline and chemically degraded soils through scented geranium *Pelargonium* sp., patent filed, NF399/00, CSIR, New Delhi). The acidity of a two volume aqueous extract of these fresh tissues was found to be more than 5 milliequivalents of sodium hydroxide (R. S. Sangwan, B. R. Tyagi and N. S. Sangwan, 2000, Ecological method of phytoremediation of alkaline and chemically degraded soils through scented geranium *Pelargonium* sp. The U.S. patent application Ser. No. 09/776,502 for the same is recently allowed.

OBJECTS OF THE PRESENT INVENTION

The main object of the present invention is to develop a methodology for proteins profiling of plant Scented Geranium (*Pelargonium* sp).

Another main object of the present invention is to develop a methodology for proteins profiling of hyper acidic parts of plant Scented Geranium (*Pelargonium* sp).

Yet another object of the present invention is to develop compositions for high degree of protein extraction from plant Scented Geranium (*Pelargonium* sp).

Still another object of the present invention is to develop compositions for high degree of protein extraction from hyper acidic parts of plant Scented Geranium (*Pelargonium* sp).

Still another object of the present invention is to determine enzymatic activity of various proteins of said plant.

Still another object of the present invention is to develop polypeptide profiling of of proteins of said plant.

SUMMARY OF THE PRESENT INVENTION

The present invention relates to a method for profiling of protein extract from hyper-acidic aerial parts of plant Scented Geranium (*Pelargonium* sp.), said method comprising steps of selecting effective extraction medium, with extraction medium consisting of 0.2 M sodium carbonate increasing percentage extract by about 600%, selecting effective medium to determine polypeptide pattern in said extract, with polypeptide pattern medium consisting of Sodium Carbonate ranging between 0.2 to 0.4M, and 0.2 M Sodium Carbonate along with 50% dimethylsulfoxide, selecting effective media to determine enzyme multimolecular forms in said extract, with enzyme multimolecular forms media consisting of 0.2M Tris-HCl buffer at pH 7.5, and optionally 50% dimethylsulfoxide; Sodium Carbonate at concentration ranging between 0.2 to 0.4M and optionally 50% dimethylsulfoxide, and using biochemical and biophysical techniques comprising gel electrophoresis, spectrophotometry, centrifugation, protein estimation in said method to determine quantitative, qualitative, structural and functional facets of the proteins from said extract, and extraction compositions thereof.

DETAILED DESCRIPTION OF THE PRESENT INVENTION

Accordingly, present invention relates to a method for profiling of protein extract from hyper-acidic aerial parts of plant Scented Geranium (*Pelargonium* sp.), said method comprising steps of selecting effective extraction medium, with extraction medium consisting of 0.2 M sodium carbonate increasing percentage extract by about 600%, selecting effective medium to determine polypeptide pattern in said extract, with polypeptide pattern medium consisting of Sodium Carbonate ranging between 0.2 to 0.4M, and 0.2 M Sodium Carbonate along with 50% dimethylsulfoxide, selecting effective media to determine enzyme multimolecular forms in said extract, with enzyme multimolecular forms media consisting of 0.2M Tris-HCl buffer at pH 7.5, and optionally 50% dimethylsulfoxide; Sodium Carbonate at concentration ranging between 0.2 to 0.4M and optionally 50% dimethylsulfoxide, and using biochemical and biophysical techniques comprising gel electrophoresis, spectrophotometry, centrifugation, protein estimation in said method to determine quantitative, qualitative, structural and functional facets of the proteins from said extract, and extraction compositions thereof.

In a further embodiment of the present invention, a composition useful for acidity neutralizing and profiling of protein extract from hyper acidic parts of plant Scented Geranium (*Pelargonium* sp.) of pH about 3.0, said composition comprising about 0.2 M Sodium Carbonate, and optionally about 50% dimethylsulfoxide (v/v) and showing increase in percentage protein extraction by about 600%, wherein final pH of said composition in said extract is ranging between 6.5 to 8.0.

In a further embodiment of the present invention, a composition useful for acidity neutralizing and profiling of protein extract from hyper acidic parts of plant Scented Geranium (*Pelargonium* sp.) of pH about 3.0, said composition comprising about 0.2 M Tris-HCl buffer, about 0.2 M Sodium Carbonate, with pH about 7.5 and showing increase in percentage protein extraction by about 300%, wherein final pH of said composition in said extract is ranging between 5.5 to 6.5.

In a further embodiment of the present invention, a composition useful for acidity neutralizing and profiling of protein extract from hyper acidic parts of plant Scented Geranium (*Pelargonium* sp.) of pH about 3.0, said composition comprising about 0.2 M Tris-HCl, and about 50% dimethylsulfoxide (v/v) with pH about 7.5 and showing increase in percentage protein extraction by about 300%, wherein pH of said composition in said extract is ranging between 6.0 to 7.0.

In an embodiment of the present invention, a method for profiling of protein extract from hyper acidic parts of plant Scented Geranium (*Pelargonium* sp.) of pH about 3.0.

In another embodiment of the present invention, homogenizing the said hyper acidic parts of plant using buffers comprising acidity-neutralizing salts and acidity sequestering compounds.

In yet another embodiment of the present invention, centrifuging the said homogenate for about 30 minutes, In still another embodiment of the present invention, obtaining said protein extract in supernatant.

In still another embodiment of the present invention, estimating obtained aqueous protein extract by conventional method.

In still another embodiment of the present invention, calculating enzymatic activity and enzyme-kinetics of peroxidase in said extract spectrophometerically.

In still another embodiment of the present invention, mixing aqueous protein extract of step (d) with sodium dodecyl sulfate-polyacrylamide (SDS) sample buffer.

In still another embodiment of the present invention, boiling the said mixture for time duration ranging between 1–10 minutes.

In still another embodiment of the present invention, cooling the boiled mixture immediately.

In still another embodiment of the present invention, electrophorizing the said mixture using sodium dodecyl sulfate-polyacrylamide polyacrylamide gel electrophoresis (SDS-PAGE).

In still another embodiment of the present invention, determining polypeptide profiles of electrophorized mixture using molecular weight marker.

In still another embodiment of the present invention, incubating native polyacrylamide gel of step (i) without sodium dodecyl sulfate, using catalysis specific chromogenic reaction mixture.

In still another embodiment of the present invention, visualizing catalytic activity bands In still another embodiment of the present invention, determining enzyme multimolecular forms pattern of said protein extract.

In still another embodiment of the present invention, wherein said plant is hyper acidic at aerial plant parts.

In still another embodiment of the present invention, wherein aerial parts of the said plant are selected from a group comprising leaf, sepal, and petal.

In still another embodiment of the present invention, wherein selecting acidity-neutralizing salts and acidity sequestering compounds from a group comprising carbonates, bicarbonates, ammoniates, and dimethylsulfoxide.

In still another embodiment of the present invention, wherein homogenizing said plant parts preferably manually.

In still another embodiment of the present invention, wherein homogenizing said plant parts at room temperature or at refrigerated conditions ranging between 0 to 4° C.

In still another embodiment of the present invention, wherein centrifuging said homogenate at a rate ranging between 7,000×g to 14,000×g.

In still another embodiment of the present invention, wherein centrifuging said homogenate at room temperature or at refrigerated conditions ranging between 0 to 4° C.

In still another embodiment of the present invention, wherein ratio of protein aqueous extract to sodium dodecyl sulfate ranging between 1:5 to 5:1.

In still another embodiment of the present invention, wherein boiling said mixture in waterbath.

In still another embodiment of the present invention, wherein electrophoresis gel-staining dyes are selected from a group comprising Coomassie Brilliant blue R-250, and silver stain.

In still another embodiment of the present invention, wherein SDS-PAGE is of both one dimension and 2 dimension types.

In still another embodiment of the present invention, wherein polypeptide pattern buffer medium is selected from a group comprising (a) Sodium Carbonate ranging between 0.2 to 0.4M, (b) Sodium Carbonate ranging between 0.2 to 0.4M and dimethylsulfoxide ranging between 10–50% (v/v), (c) about 0.2M Tris-HCl buffer at pH ranging between 7.0–8.0, and (d) about 0.2M Tris-HCl buffer at pH ranging between 7.0–8.0 and dimethylsulfoxide at concentration ranging between 10–50% (v/v).

In still another embodiment of the present invention, wherein catalysis specific chromogenic reaction mixture for esterase catalytic activity is comprising about 2 mM alpha-napthylacetate, about 2 mM beta-napthylacatate, about 1 mM Fast Blue salt, in about 0.1 M phosphate buffer at about 6.5 pH.

In still another embodiment of the present invention, wherein catalysis specific chromogenic reaction mixture for glutamate oxaloactate transaminase (GOT) catalytic activity is comprising about 2 mM pyridoxal phosphate, about 4 mM L-aspartic acid, about 4.3 mM alpha-ketoglutaric acid and about 5.4 mM Fast Blue BB salt in about 0.1 M tris-HCl at about 8.5 pH.

In still another embodiment of the present invention, wherein said method is used for proteomics in plant and animal tissues of hyper acidic nature.

In still another embodiment of the present invention, wherein homogenizing said plant with buffers selected from a group comprising (a) about 0.2 M Tris solution, pH about 10.5 and above, (b) about 0.2 M Tris-HCl buffer, pH about 7.5 containing about 0.2 M Sodium Carbonate, (c) about 0.2 M Sodium Carbonate, (d) about 0.2 M Tris-HCl, pH about 7.5 containing upto 50% dimethylsulfoxide (v/v), and (e) about 0.2 M sodium carbonate containing upto 50% dimethylsulfoxide (v/v).

In still another embodiment of the present invention, wherein homogenization buffer is supplement with glycerol ranging between 7 to 14%.

In still another embodiment of the present invention, wherein buffer composition comprising about 0.2 M Sodium Carbonate showing increase in percentage protein extract by about 600%.

In still another embodiment of the present invention, wherein buffer composition comprising about 0.2 M sodium carbonate, about 50% dimethylsulfoxide (v/v) showing increase in percentage protein extract by about 600%.

In still another embodiment of the present invention, wherein buffer composition comprising about 0.2 M Tris-HCl buffer, about 0.2 M Sodium Carbonate, with pH about 7.5 showing increase in percentage protein extract by about 300%.

In still another embodiment of the present invention, wherein composition comprising about 0.2 M Tris-HCl, and about 50% dimethylsulfoxide (v/v) with pH about 7.5 showing increase in percentage protein extract by about 300%.

In still another embodiment of the present invention, wherein SDS-PAGE has discontinuous system with stacking and resolving gel in vertical electrophoresis system.

In still another embodiment of the present invention, wherein concentration of stacking gel ranging between 2 to 6% (T).

In still another embodiment of the present invention, wherein concentration of resolving gel ranging between 10 to 18% (T).

Further, the present invention provides processes for proteomics of scented geranium (*Pelargonium* sp.) tissues which comprises extraction of the specified tissues (leaf, sepal and petal), by hand homogenization (at room temperature or cold conditions of 0 to 4° C. (depending upon the end objective in proteomic work) with half to one volume (1 g fresh weight into 0.5 to 0.0 ml or more depending upon nature and state of tissue) of glycerol supplemented (10%) appropriate buffer (like Tris-HCl) or distilled water containing upto 0.4 M concentration (depending upon the application of acidity-neutralizing salt like carbonates or bicarbonates etc. or in presence of appropriate concentration (upto 50%) of acidity sequestering (like forming complexes with organic acids) compounds like dimethyl sulfoxide followed centrifugation at 10,000×g for 30 min in a centrifuge at ambient temperature or refrigerated conditions of 0 to 4° C. (depending upon the end objectives in the proteomic work) to recover the aqueously isolated proteins in the supernatant which can be further used satisfactorily for the various proteomic works like having a true quantitative measure of protein concentration, measurement of catalytic activities of enzymes and other enzymatic/protein physico-kinetic and regulatory studies, discerning and studying multiple molecular forms of enzymes including their post-native PAGE run in situ catalytic localization and profiling of polypeptide patterns through denaturing or otherwise electrophoretic techniques employing standard techniques.

In an embodiment of the present invention the compatible cellular acidity nullifying process may be used for carrying out proteomic works on the scented geranium (*Pelargonium* sp. plant indispensably initiating with quantitative recovery of protein complement from tissue(s).

In another embodiment of the present investigation the tissue homogenization medium may be supplemented (alternatively and/or additionally depending upon the specific objectives) with compounds like dimethyl sulfoxide to accomplish the proteomic work on scented geranium.

In yet another embodiment of the present investigation the processes provide thematic solutions for various genre of proteomic analyses/examinations ranging from quantitative estimation to catalytic activity measurements and achievements on electrophoretic displays of protein/enzyme/polypeptide patterns in the designated tissues of scented geranium.

In still another embodiment of the present invention, this acidity appears to be much more than that can be taken care of by the usual buffered extraction medium. Consequently, the strikingly low pH conditions existent in the homogenate not only drastically restrict the extraction (via profound diminution of aqueous solubility) of the proteins but also qualitatively and/or quantitatively alter its native physico-chemical (including catalytic/enzymatic) attributes.

In still another embodiment of the present invention, the inclusion of appropriate levels of compatible acidity neutralizing (like carbonates, bicarbonates, ammonia/ammoniates etc. etc.) or complexing (like dimethyl sulfoxide) chemicals in the tissue extraction medium can help obviate the impediments in carrying out the proteomic work on the plant/plant parts.

In still another embodiment of the present invention, so far, troubles in isolating proteins from plant samples have been encountered and technogolically addressed from the standpoint of preponderance of proteases, polyphenols etc. Tissue hyper-acidity of this order is quite rare in crop plants. Accordingly, the problem of aqueous isolation of proteins from such tissues might have been scantly encountered.

In still another embodiment of the present invention, even in positive cases, change of the test tissue in the plant might have left the thematic problem unsolved. Thus, the invention provides novel processes for facilitating proteomic studies/analyses in the hyper-acidic tissues of scented geranium (*Pelargonium* sp.).

BRIEF DESCRIPTION OF THE ACCOMPANYING DRAWINGS

FIG. 1 shows SDS-PAGE (Coomassie stained) gel of scented geranium leaf tissue protein preparations (A–E). Lane 1, A; Lane 2, B; Lane 3, C; Lane 4, D; Lane 5, E, Lane 6, empty; Lane 7, molecular weight markers (phosphorylase b-66000, BSA-66000, ovalbumin -43000, carbonic anhydrous-29000, STI-20100, lysozyme-14300).

Figure 2:

FIG. 2 shows SDS-PAGE (silver stained) gel of scented geranium leaf tissue protein preparations (A–C). Lane 1, A; Lane 2, B; Lane 3, C; Lane 4, empty; Lane 5, molecular weight markers (phosphorylase b-66000, BSA-66000, ovalbumin-43000, carbonic anhydrous-29000, STI-20100, lysozyme-14300).

Figure 3:
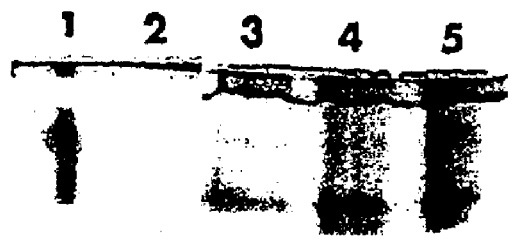

FIG. 3 shows Native PAGE and in situ staining of esterase catalytic activity in geranium leaf tissue preparations (A–E). Lane 1, A; Lane 2, B; Lane 3, C; Lane 4, D; Lane 5, E, The reaction mixture (12.5 ml) contained 2 mM a-napthylacetate, 2 mM p-napthylacetate, 1 mM Fast Blue RR salt in 0.1 M phosphate buffer (pH 6.5).

Figure 4:
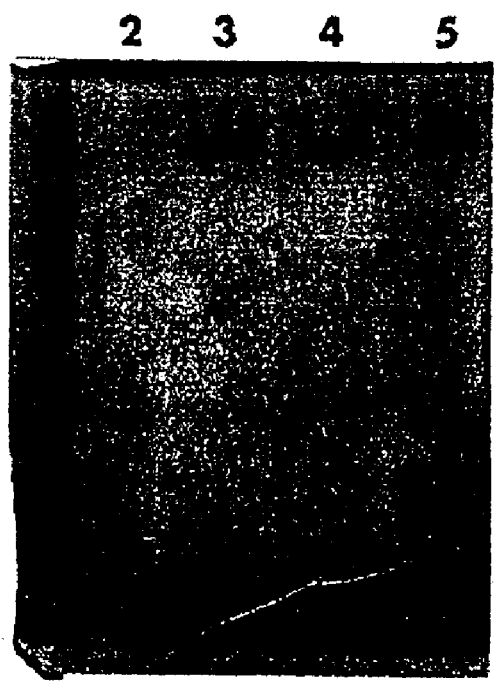

FIG. 4 shows Native PAGE and in situ staining of glutamate oxaloacetate transaminase (GOT) catalytic activity in geranium leaf tissue preparations (A–E). Lane 1, A; Lane 2, B; lane 3, C; Lane 4, D; Lane 5, E. The reaction mixture (12.5 ml) contained 2 mM pyridoxal phosphate, 4 mM L-aspartic acid, 4.3 mM a-ketoglutaric acid and 5.4 mM Fast Blue BB salt in 0.1 MTris-HCl (pH8.5).

EXAMPLES

The following examples are given by way of illustration of the present invention and should not be construed to limit the scope of the present invention:

Example 1

One gram of fresh leaf tissue from cultivar 'Bourbon' of scented geranium (*Pelargonium* sp.) was subjected to aqueous isolation of soluble proteins by hand homogenization of the tissue with half volume (0.5 ml extraction medium per 1.0 g of fresh tissue) of (A) 0.2 M Tris-HCl buffer, pH 7.5 or (B) double distilled water or (C) 0.2 M Tris solution, pH above 10.5 or (D) 0.2 M Tris-HCl buffer, pH 7.5 containing 0.2 M $Na_2CO_3$ or (E) 0.2 M $Na_2CO_3$ or (F) 0.2 M Tris-HCl, pH 7.5 containing 50% dimethylsulfoxide (v/v) or (G) 0.2 M Na2COa containing 50% dimethylsulfoxide (v/v) in an all glass pestle and mortar at room temperature. The tissue homogenate was centrifuged at 10,000×g for 30 min and the supernatant was collected. The pH of the supernatant was noted. 400 jal of 12% trichloroacetic acid (TCA) was added to 400 fil of supernatant in each case in a microcentrifuge tube and allowed to stand for 30 min. The contents were centrifuged in a microcentrifuge and the protein sediment was retained. The protein was dissolved in 400 jal of 0.1 N NaOH solution. The protein was quantified, using 100 to 200 ^1 aliquot of the solution, employing standard Lowry method (O. H Lowry, N. J. Rosebrough, A. L. Farr and R. J. Randall, 1951, J. Biol. Chem. 193: 265). The absorbance after color development was read at 660 nm. The protein was quantified using BSA as standard. The results are tabulated below:

TABLE 1

| Treatment | pH of extract | Protein extracted (mg/g fresh weight) | Comparative performance [% of control] | Comparative status as percentage of maxima |
|---|---|---|---|---|
| A [Control] | 3.0 | 82.9 | 100.0 | 15.29 |
| B | 3.0 | 87.7 | 105.8 | 16.17 |
| C | 4.5 | 68.8 | 83.0 | 12.69 |
| D | 6.0 | 293.4 | 353.9 | 54.12 |
| E | 7.5 | 542.1 | 653.9 | 100.0 |
| F | 6.5 | 304.0 | 366.7 | 56.07 |
| G | 7.0 | 497.4 | 600.0 | 91.75 |

Evidently, the invented technological processes (like treatments E and G) lead to substantial isolation of proteins from the tissue. Comparatively, it provides up to 6.5 times enhanced recovery of tissue protein. It is of quantitative and qualitative essence in proteomic works and analyses.

Example 2

One gram of fresh leaf tissue from cultivar 'Bourbon' of scented geranium (*Pelargonium* sp.) was subjected to aqueous isolation of soluble proteins by hand homogenization of the tissue with half volume (0.5 ml extraction medium per 1.0 g of fresh tissue) of chilled extraction media: (A) 0.2 M Tris-HCl buffer, pH 7.5 or (B) 0.2 M Tris solution, pH above 10.5 or (C) 0.2 M Tris-HCl buffer, pH 7.5 containing 0.2 M $Na_2CO_3$ or (D) 0.2 M $Na_2CO_3$ or (E) 0.2 M Tris-HCl, pH 7.5 containing 50% dimethylsulfoxide (v/v) or (F) 0.2 M $Na_2CC>3$ containing 50% dimethylsulfoxide (v/v) in an all glass pestle and mortar at 0 to 4° C. The tissue homogenate was centrifuged at 10,000×g for 30 min at 0 to 4° C. in a refrigerated centrifuge and the supernatant was collected and used as enzyme extract to measure the catalytic level of peroxidase. The catalytic activity was measured spectrophotometrically at 30° C., using guaiacol as substrate, following the rate of increase in absorbance at 470 rim. The standard assay mixture (3.0 ml) consisted of 5 ml of 0.1 M acetate buffer (pH 5.5), 0 ml of 0.0 mM guaiacol, 300 ^1 of 1.3 mM $H_2O_2$, 10 to 50 ^1 (depending upon the catalytic aliquot of the enzyme preparation (EP), and distilled water to make up the volume. The results are tabulated below.

TABLE 2

| Treatment | $\Delta A_{470}$/ 50 µl EP Min.$^{-1}$ | Catalytic activity Monitored Units* per | | Comparative performance [% of control Activity; per g fresh weight] | Comparative status as % of maxima (with data on fresh weight basis) |
|---|---|---|---|---|---|
| | | gm fresh Weight | mg protein | | |
| A [Control] | 0.0001 | 0.1 | 1.206 | 100 | 0.30 |
| B | 0.0016 | 1.6 | 23.256 | 1600 | 4.73 |

TABLE 2-continued

| | $\Delta A_{470}/$ 50 µl EP Min.$^{-1}$ | Catalytic activity Monitored Units* per | | Comparative performance [% of control | Comparative status as % of maxima |
|---|---|---|---|---|---|
| Treatment | | gm fresh Weight | mg protein | Activity; per g fresh weight] | (with data on fresh weight basis) |
| C | 0.0193 | 19.3 | 65.781 | 19300 | 57.10 |
| D | 0.0320 | 32.0 | 59.030 | 32000 | 94.67 |
| E | 0.0338 | 33.8 | 111.184 | 33800 | 100.0 |
| F | 0.0297 | 29.7 | 59.710 | 29700 | 87.87 |

One unit of enzyme activity is defined as equal to an increase in absorbance @ 0.010 per min.

Evidently, for realistic assessment of the catalytic activities of enzymes of scented geranium tissue, the invented technology is a thematic prerequisite. Appropriate application in an enzyme-specific manner may require process standardization/optimization as per requirement imposed by the enzyme(s) or the experimenter.

Example 3

One gram of fresh leaf tissue from cultivar 'Bourbon' of scented geranium (*Pelargonium* sp.) was subjected to aqueous isolation of soluble proteins by hand homogenization of the tissue with half volume (0.5 ml extraction medium per 1.0 g of fresh tissue) of chilled extraction media (A) 0.2 M Tris-HCl buffer, pH 7.5 or (B) 0.2 M Tris-HCl, pH 7.5 containing 50 % dimethylsulfoxide (v/v) or (C) 0.2 M $Na_2CO_3$ or (D) 0.4 M $Na_2CO_3$ (E) 0.2 M Na2COs containing 50% dimethylsulfoxide (v/v) in an all glass pestle and mortar at 0 to 4° C. The tissue homogenate was centrifuged at 10,000×g for 30 min at 0 to 4° C. in a refrigerated centrifuge and the supernatant was collected and used for carrying out sodium dodecyl sulfate-polyacrylamide gel electrophoresis (SDS-PAGE) to display polypeptide profiles in the tissue extract. For this, 100 µl of the extract was mixed with equal volume of SDS sample buffer in a microcentrifuge tube and the contents were kept in a boiling waterbath for three minutes. The samples were quick-cooled on ice and stored at −20° C. until used for electrophoresis. The denaturing SDS-PAGE was carried out using a discontinuous system of stacking and resolving gel in a vertical electrophoresis system (Mini Protean-II, Bio Rad). Equal volumes (25 fil each for Coomassie staining) of each sample preparation were loaded in the wells and a standard molecular weight marker mixture was co-electrophorsed in each gel. The polymer concentration in the gel was 4.0% (T) in stacking gel and 14.0% (T) resolving gel. Bromophenol blue was used as the tracking dye. The electrophoresis was conducted at constant voltage (150volts for sample movement through stacking gel and 100 volts for the resolving gel). After the electrophoresis was over, the stacking gel region was sliced out with a razor and the resolving gel was stained for protein profile using Coomassie brilliant blue R-250. Some of the representative gels displaying proteomic patterns are presented below. (FIG. 1)

Evidently, proteomic (polypeptide pattern) solutions for the scented geranium tissue are only feasible using the extraction media (particularly the treatments like C, D and E) constituting the thematic technological domains of this invention. This being the key feature, applies to both 1-D as well as 2-D proteomics for the plant species.

Example 4

One gram of fresh leaf tissue from cultivar 'Bourbon* of scented geranium (*Pelargonium* sp.) was subjected to aqueous isolation of soluble proteins by hand homogenization of the tissue with half volume (0.5 ml extraction medium per 1.0 g of fresh tissue) of chilled extraction media: (A) 0.2 M Tris-HCl buffer, pH 7.5 or (B) 0.2 M Tris-HCl, pH 7.5 containing 50% dimethylsulfoxide (v/v) or © 0.2 M Na2COs in an all glass pestle and mortar at 0 to 4° C. The tissue homogenate was centrifuged at 10,000× g for 30 min at 0 to 4° C. in a refrigerated centrifuge and the supenatant was collected and used for carrying out sodium dodecyl sulfate-polyacrylamide gel electrophoresis (SDS-PAGE) to display polypeptide profiles in the tissue extract For this, 100 |iil of the extract was mixed with equal volume of SDS sample buffer in a microcentrifuge tube and the contents were kept in a boiling waterbath for three minutes.

The samples were quick-cooled on ice and stored at −20° C. until used for electrophoresis. The denaturing SDS-PAGE was carried out using a discontinuous system of stacking and resolving gel in a vertical electrophoresis system (Mini Protean-II, Bio Rad). Equal volumes (10 jjl) of each sample preparation were loaded in the wells and a standard molecular weight marker mixture was co-electrophorsed in each gel. The polymer concentration in the gel was 4.0% (T) in stacking gel and 14.0% (T) resolving gel. Bromophenol blue was used as the tracking dye. The electrophoresis was conducted at constant voltage (150 volts for sample movement through stacking gel and 100 volts for the resolving gel). After the electrophoresis was over, the stacking gel region was sliced out with a razor and the resolving gel was stained for protein profile using silver staining protocol (nondiamine chemical development of protein stains). Some of the representative gels displaying proteomic patterns are presented below. (FIG. 2)

Evidently, even employing silver staining-assisted detection, proteomic (polypeptide pattern) solutions for the scented geranium tissue are reasonably feasible using the extraction media (particularly like treatments C) constituting the thematic technological domains of this invention. This being the key feature applies to both 1-D as well as 2-D proteomics for the plant species.

Example 5

One gram of fresh leaf tissue from cultivar 'Bourbon* of scented geranium (*Pelargonium* sp.) was subjected to aqueous isolation of soluble proteins by hand homogenization of the tissue with half volume (0.5 ml extraction medium per 1.0 g of fresh tissue) of chilled extraction media: (A) 0.2 M Tris-HCl, pH 7.5 containing 50% dimethylsulfoxide (v/v) or (B) 0.2 M Tris-HCl buffer, pH 7.5 or (C) 0.2 M $Na_2CO_3$ or (D) 0.4 M $Na_2CO_3$ (E) 0.2 M Na2CC>3 containing 50% dimethylsulfoxide (v/v) in an all glass pestle and mortar at 0 to 4° C. The tissue homogenate was centrifuged at 10,000×g for 30 min at 0 to 4° C. in a refrigerated centrifuge and the supernatant was collected and used for carrying out enzyme multiple molecular forms patterning in the native polyacrylamide gel. The non-denaturing polyacrylamide gel electrophoresis was carried out using a discontinuous system of stacking and resolving gel in a vertical electrophoresis system (Mini Protean-II Bio Rad). Equal volumes (25 jal) of each sample preparation were loaded in the wells. The polymer concentration in the gel was 4.0% (T) stacking gel and 14.0% (T) resolving gel. Bromophenol blue was used as the tracking dye. The electrode buffers were pre-cooled to 4° C. and the electrophoresis was conducted at 0 to 4° C. at constant voltage (150 volts for sample movement through stacking gel and 100 volts for the resolving gel). After the electrophoresis was over, the stacking gel region was sliced out with a razor and the resolving gel was subjected to in situ localization of catalytic activity bands by incubating the gels with the catalysis specific chromogenic reaction mixture at 37° C. On visualization of catalytic activity bands, the isozymic patterns were image captured on a gel documentation system (pdi Inc., USA) using an optically enhanced scanner (420 oe, pdi Inc.) using Diversity Database™. Some of the representative enzyme/isozymes localized gels, displaying in situ catalytic patterns, are presented below.

Evidently, proteomic (enzymatic) solutions for the scented geranium tissue are only feasible using the extraction media constituting the thematic technological domains of this invention.

The Main Advantages of the Present Invention:
1. It provides feasibilities of isolating soluble proteins aqueously from the recalcitrant tissues of scented geranium. As a matter of fact, these tissues are most important from the commercial as well as academic interest.
2. It enables carrying out proteomics of the tissues which is key to comprehend functional genomics.
3. It facilitates isolation and identification of signal polypeptides/proteins from the tissues in relation to intrinsic and extrinsic factors ranging development to modulation etc.
4. The processes are useful for carrying enzyme/isozymes/protein/polypeptide patterning for diverse applications including diversity assessment, pedigree analysis, phylogenetic, genotype/cultivar diagnosis, inheritance, hybrid assessment, and other applications like protein based co-dominant marking (isozymes, antibody probed polypeptides etc.) etc.
5. The processes offer to help metabolic/enzymological studies, important to understand the mechanism and regulation of primary and secondary metabolic pathways. This also forms the basis of their modulation.
6. It can be used as an efficient tool to study expression (at translation or post translation level) of native (endogenous) or alien gene(s) (transgene) etc.

What is claimed is:

1. A method for profiling of protein extract from hyper acidic parts of scented Geranium plant (*Pelargonium* sp.) said hyper acidic parts being of pH about 3.0, said method comprising:
   (a) homogenizing the hyper acidic parts of the plant in buffers comprising acidity-neutralizing salts and acidity sequestering compounds,
   (b) centrifuging the homogenate for about 30 minutes,
   (c) obtaining supernatant, from the centrifugation of part (b) wherein said supernatant is the protein extract
   (d) optionally centrifuging the supernatant of part (c) to obtain a protein sediment and estimating the amount of protein sediment obtained,
   (e) calculating enzymatic activity and enzyme-kinetics of peroxidase in said extract of part (c) spectrophometerically,
   (f) mixing the protein extract of step (c) with sodium dodecyl sulfate-polyacrylamide (SDS) sample buffer,
   (g) boiling the mixture of part (f) for a time ranging between 1–10 minutes,
   (h) cooling the boiled mixture immediately,
   (i) electrophorizing the mixture part (h) using sodium dodecyl sulfate-polyacrylamide polyacrylamide gel electrophoresis (SDS-PAGE),
   (j) determining polypeptide profiles of the electrophorized mixture using molecular weight markers,
   (k) electrophorizing the mixture of step (h) using polyacrylamide gel electrophoresis and using a catalysis specific chromogenic reaction mixture,
   (l) visualizing catalytic activity bands, and
   (m) determining enzyme patterns of said protein extract.

2. A method as claimed in claim 1, wherein said hyper acidic parts are arial parts.

3. A method as claimed in claim 2, wherein the arial parts of the plant are selected from the group consisting of leaf, sepal, and petal.

4. A method as claimed in claim 1, wherein said acidity-neutralizing salts and acidity sequestering compounds are selected from the group consisting of carbonates, bicarbonates, ammoniates, and dimethylsulfoxide.

5. A method as claimed in claim 1, wherein homogenizing said plant parts is performed manually.

6. A method as claimed in claim 1, wherein homogenizing said plant parts is carried out at room temperature or at temperatures ranging between 0 to 4° C.

7. A method as claimed in claim 1, wherein centrifuging said homogenate occurs at a rate ranging between 7,000×g to 14,000×g.

8. A method as claimed in claim 1, wherein centrifuging said homogenate occurs at room temperature or at temperatures ranging between 0 to 4° C.

9. A method as claimed in claim 1, wherein in step (f) the ratio of protein extract to sodium dodecyl sulfate ranges between 1:5 to 5:1.

10. A method as claimed in claim 1, wherein said boiling occurs in a waterbath.

11. A method as claimed in claim 1, wherein the gel is stained using a dye selected from the group consisting of Coomassie Brilliant blue R-250, and silver stain.

12. A method as claimed in claim 1, wherein SDS-PAGE is a one dimension or 2 dimension type.

13. A method as claimed in claim 1, wherein the buffer is selected from the group consisting of (a) sodium carbonate ranging between 0.2 to 0.4 M, (b) sodium carbonate ranging between 0.2 to 0.4 M and dimethylsulfoxide at a concentration ranging between 10–50% (v/v), (c) about 0.2 M Tris-HCl buffer at pH ranging between 7.0–8.0 and (d) about 0.2 M Tris-HCl buffer at pH ranging between 7.0–8.0 and dimethylsufoxide at a concentration ranging between 10–50% (v/v).

14. A method as claimed in claim 1, wherein, the catalysis specific chromogenic reaction mixture is specific for esterase catalytic activity and comprises about 2 mM alpha-napthylacetate, about 2 mM beta-napthylacatate, about 1 mM Fast Blue salt, in about 0.1 M phosphate buffer at about 6.5 pH.

15. A method as claimed in claim 1, wherein, catalysis specific chromogenic reaction mixture is specific for glutamate oxaloacetate transaminase (GOT) catalytic activity and comprises is about 2 mM pyridoxal phosphate, about 4 mM L-aspartic acid, about 4.3 mM alpha-ketoglutaric acid and about 5.4 mM Fast Blue BB salt in about 0.1 M tris-HCl at about 8.5 pH.

16. A method as claimed in claim 1, wherein said plant is homogenized with buffers selected from the group consisting of (a) about 0.2 M Tris solution, pH about 10.5 and above, (b) about 0.2 M Tris-HCl buffer, pH about 7.5 containing about 0.2 M sodium carbonate, (c) about 0.2 M sodium carbonate, (d) about 0.2 M Tris-HCl, pH about 7.5 containing upto 50% dimethylsulfoxide (v/v), and (e) about 0.2 M sodium carbonate containing upto 50% dimethylsulfoxide (v/v).

17. A method as claimed in claim 16, wherein the buffer further comprises glycerol ranging between 7 to 14%.

18. A method as claimed in claim 16, wherein use of an acidity-neutralizing buffer composition comprising about 0.2 M carbonate results in an increase of about 600% in the amount of protein extracted.

19. A method as claimed in claim 16, wherein use of an acidity-neutralizing buffer composition comprising about 0.2 M sodium carbonate, and about 50% dimethylsulfoxide (v/v) results in an increase of about 600% in the amount of protein extracted.

20. A method as claimed in claim 16, wherein use of an acidity-neutralizing buffer composition comprising about 0.2 M Tris-HCl buffer, about 0.2 M sodium carbonate at a pH of about 7.5 results in about a 300% increase in the amount of protein extracted.

21. A method as claimed in claim 16, wherein use of an acidity-neutralizing buffer composition comprising about 0.2 M Tris-HCl, and about 50% dimethylsulfoxide (v/v) with pH about 7.5 results in about a 300% increase in the amount of protein extracted.

22. A method as claimed in claim 1, wherein SDS-PAGE has discontinuous system with stacking and resolving gel in vertical electrophoresis system.

23. A method as claimed in claim 22, wherein the concentration of the stacking gel is in the range between 2 to 6% (T).

24. A method as claimed in claim 22, wherein the concentration of the resolving gel is in the range between 10 to 18% (T).

* * * * *